United States Patent
Reid, Jr.

(10) Patent No.: US 6,613,007 B1
(45) Date of Patent: Sep. 2, 2003

(54) MULTILAYER COMPRESSION STOCKING SYSTEM AND METHOD

(75) Inventor: Lawrence G. Reid, Jr., Germanton, NC (US)

(73) Assignee: Carolon Company, Rural Hall, NC (US)

( * ) Notice: Subject to any disclaimer, the term of this patent is extended or adjusted under 35 U.S.C. 154(b) by 0 days.

(21) Appl. No.: 09/602,366

(22) Filed: Jun. 23, 2000

Related U.S. Application Data

(60) Provisional application No. 60/141,085, filed on Jun. 25, 1999.

(51) Int. Cl.[7] ............................ A61F 13/00; A61F 13/08
(52) U.S. Cl. ........................................... 602/75; 602/62
(58) Field of Search ................................. 602/5, 60–63, 602/74–77; 128/882; 2/239–242; 66/178 R, 183, 184

(56) References Cited

U.S. PATENT DOCUMENTS

| | | | | | |
|---|---|---|---|---|---|
| 858,006 | A | * | 6/1907 | Lum | 2/239 |
| 1,257,643 | A | * | 2/1918 | Smith | 2/239 |
| 1,775,714 | A | * | 9/1930 | Bass | 2/239 |
| 1,833,163 | A | * | 11/1931 | Ischinger | 2/239 |
| 3,856,008 | A | * | 12/1974 | Fowler | 602/62 |
| 4,172,456 | A | * | 10/1979 | Zens | 602/62 |
| 4,502,301 | A | * | 3/1985 | Swallow et al. | 66/178 R |
| 4,513,740 | A | * | 4/1985 | Westlake | 602/62 |
| 5,006,401 | A | * | 4/1991 | Frank | 428/231 |
| 5,338,290 | A | * | 8/1994 | Aboud | 602/75 |
| 5,425,702 | A | * | 6/1995 | Carn et al. | 602/62 |
| 5,439,438 | A | * | 8/1995 | Ersfeld | 602/3 |
| 5,675,992 | A | * | 10/1997 | Wrightenberry | 66/178 R |
| 5,814,003 | A | * | 9/1998 | Knox et al. | 602/63 |
| 6,248,043 | B1 | * | 6/2001 | Morton | 482/11 |
| 6,338,723 | B1 | * | 1/2002 | Carpenter | 602/75 |

\* cited by examiner

*Primary Examiner*—Denise M. Pothier
(74) *Attorney, Agent, or Firm*—Kilpatrick Stockton LLP

(57) ABSTRACT

A multilayer compression stocking or bandage system comprises a plurality of layers, including an underlayer and at least one overlayer, each of which may have predetermined amounts of compressive pressure at discrete locations. In one aspect, the underlayer has one or more alignment markings, each positioned at a different location on the underlayer to assist in aligning discrete locations of compressive pressure on the lower extremities. In another aspect, each of the layers has one or more alignment markings, each alignment marking positioned at a different location on the respective layer, and each alignment marking on a layer corresponds to a different one of the alignment markings on each other layer. When alignment markings on each layer are aligned with corresponding markings on each other layer, discrete locations of specific amounts of compressive pressure on each layer can be properly aligned, resulting in accurate higher pressures at particular anatomical locations and proper pressure gradations along the length of the leg.

40 Claims, 2 Drawing Sheets

MULTILAYER COMPRESSION STOCKING SYSTEM AND METHOD

The present application claims the benefit, under 35 U.S.C. §119, of U.S. provisional application serial No. 60/141,085, filed Jun. 25, 1999.

FIELD OF THE INVENTION

The present invention relates to elastic garments or wraps that exert a compressive force when worn. An aspect of the invention is a compression stocking useful in the prevention and/or treatment of medical conditions of the lower extremities and vascular system in the lower extremities.

BACKGROUND OF THE INVENTION

Therapeutic garments and elastic bandages that exert a compressive force are often utilized in the prevention and therapy of lower extremity vascular system disorders, such as edema, emboli, and thrombophlebitis. For example, compressive stockings are utilized to improve vascular circulation and to reduce edema and the possibility of emboli in the legs. Compression therapy is often utilized for the prevention and treatment of conditions caused by chronic venous insufficiency, including stasis ulceration in the leg. Elastic bandages, for example, have traditionally been used for compressive therapy of vascular disorders, including ulcers, of the lower extremities.

Therapeutic or compressive stockings are constructed to apply compressive pressure to a wearer's legs. Compressive pressure may be greatest at the foot and gradually decrease from the foot towards the upper, or proximal, part of the leg. Alternatively, compressive pressure may be greatest at the ankle and gradually decrease towards the upper part of the leg. The amount of compressive pressure applied depends on the particular use and needs of the wearer. In order to achieve the intended preventative and/or therapeutic effect and to avoid complications of compressive pressure intervention, compressive pressure must be applied accurately. For example, should a greater amount of compressive pressure be applied higher on the leg than lower on the leg, blood flow may be impaired with a possible tourniquet effect occurring.

Further details on therapeutic compressive stockings, their use and construction, may be found in U.S. Pat. Nos. 4,015,448, issued Apr. 5, 1977; U.S. Pat. No. 4,172,456, issued Oct. 30, 1979; U.S. Pat. No. 4,513,740, issued Apr. 30, 1985; U.S. Pat. No. 4,745,917, issued May 24, 1988; and U.S. Pat. No. 5,005,567, issued Apr. 9, 1991. The disclosure of each of these patents is hereby incorporated herein by reference.

When elastic bandages are used, the bandages are wrapped onto the leg with the greatest pressure at the foot or ankle, and compressive pressures are manually reduced as the bandages are wrapped up the leg. Applying correct pressures at particular locations, and properly graduating pressures, so as to avoid creating a tourniquet effect when wrapping elastic bandages is difficult. Elastic bandages also come in a variety of styles, with stretch characteristics varying widely from product to product, making proper application of correct compression difficult.

The compressive pressure applied by stockings at a particular anatomical location may be determined and measured by various techniques. As will be recognized in the art, there is no standardized system for testing and measuring compressive pressures. A commonly used system for measuring compressive pressures is a British system, which may be used with pressure testing equipment made by Instron and by Hatra. (See, British Standard Specification for Graduated Compression Hosiery, BS 6612: 1985.) The British system divides compressive pressures into three levels, each level being referred to as a class. In Class I, 14 to 19 mm Hg (millimeters of mercury) of compressive pressure is provided. In Class II, 18 to 25 mm Hg of compressive pressure is provided. In Class III, 24 to 35 mm Hg of compressive pressure is provided. A Class I stocking would therefore provide 14 to 19 mm Hg of compressive pressure at the point of greatest compressive pressure. A Class II stocking would provide 18 to 25 mm Hg of compressive pressure at the point of greatest compressive pressure, and a Class III stocking would provide 24 to 35 mm Hg compressive pressure at the point of greatest compressive pressure. Suggested preventative and therapeutic uses for each class of pressure are also defined by the British system. Another system for measuring compressive pressures is a German system, which may be used with testing equipment made by Holenstein. The German system categorizes compressive pressures between 20 and 30 mm Hg as Class I, between 30 and 40 mm Hg as Class II, and between 40 and 50 mm Hg as Class III. (See also, European Committee for Standardization, CEN-TC 205WG2 Medical Compression Hosiery.)

There are no recognized standards for testing elastic bandages to accurately determine compressive pressures. Pressures applied by elastic bandages have been described by the amount of stretch of the elastic material, such as 50%, 100%, and 200%. Controlling the amount of compressive pressure a bandage will exert when applied requires extensive technical knowledge of bandage stretch characteristics, as well as experience. Some elastic bandages have incorporated methods to assist a care-giver in proper application. For example, visual indicators may be used to signify the degree of stretch, and thus compressive force, provided by an elastic bandage. A continuous pattern of geometric shapes may be formed on an elastic bandage by using indicator yams or with print. Either the shape of the geometric design or the spacing between shapes in a pattern may change when tension is applied to the bandage, indicating a change in compressive force. Such designs in elastic bandages have been used to indicate compressive pressures as high as 40 to 50 mm Hg.

Compressive stockings, due to the compressive pressures they apply, are generally more difficult to place on the leg than conventional dress hosiery. To be most effective, the area or areas of the stockings having the highest compressive pressure, and thus the most difficult to apply, should be located at the feet or more distal portions of the leg, such as the ankle. Consequently, compressive stockings are often especially difficult for the elderly or persons with compromised mobility to apply to their legs. In addition, higher compressive pressures are indicated for the prevention and treatment of leg ulcerations. As a result, compressive stockings that use higher compressive pressures, such as for leg ulcerations, may be even more difficult to apply.

It has been generally found that most persons can place, or apply, Class I stockings with minimal or no assistance. However, many patients are unable to apply or remove stockings with Class II or Class III pressures without assistance by a care-giver or medical personnel. Such stockings may also be difficult for the care-giver to apply. As discussed above, compression therapy is often utilized for the prevention and treatment of ulcers, for which Class II or Class III compressive pressures may be beneficial. Often, patients suffering from leg ulcers have difficulty applying stockings with Class II or Class III compressive pressures due to age or disability, such as compromised mobility. Such patients may also have difficulty removing such stockings, particularly if they are applied by a care-giver. It may also be difficult for a care-giver to remove such stockings due to the compressive pressures involved.

For compressive therapy to be most effective, higher pressures may be required. The very high pressures that may be required for both prevention and therapy may preclude use of a stocking, as construction of a stocking having such higher compressive force may cause the stocking to be too tight to apply over the heel of a person's foot. As an alternative, high pressure elastic bandages which can be applied directly to a leg, without placement over the foot as with compressive stockings, may be used. Pressures higher than those supplied by a stocking can be applied by an elastic bandage. Using a high pressure elastic bandage, a leg is generally wrapped by a care-giver, rather than by a patient, as applying desired pressures with proper pressure graduation up the leg requires training and experience. Because of the difficulty of properly applying elastic bandages, they may be left on a patient for longer periods than a compressive stocking.

Higher compressive pressures and a wider range of pressures can be obtained by utilizing multiple stockings in layers. The layering of compressive pressures will produce a cumulative pressure effect. Layering a stocking that provides 10 mm Hg pressure with a Class I stocking would produce a stocking with Class II pressure. Layering a stocking that provides 10 mm Hg pressure with a Class II stocking would produce a stocking with Class III pressure. Layering two Class I stockings may produce Class II compressive pressures. Similarly, applying a Class II stocking over a Class I stocking may produce Class III compressive pressures. Layering of stockings allows the use of higher compressive pressures indicated for certain medical conditions. Since compression stockings are constructed having specific compressive pressures, layering of stockings to achieve specific higher, cumulative, compressive pressures eliminates the uncertainty of pressures resulting from application of elastic bandages. In addition, using multiple layers of compression stockings, patients and care-givers can apply a wide variety of accurate pressures.

However, there are many problems associated with layering multiple stockings. One problem is that it is difficult to coordinate the compressive pressures applied by each stocking to achieve a desired increased pressure at particular anatomical locations on the lower extremities. Should the areas of compressive pressure not align correctly, it is possible that the area of highest pressure may be on a more proximal, and thus undesired, area of the leg, and a tourniquet effect may result. Further, any ridges or wrinkles in the stockings, introduced either during construction of the stockings or as the stockings are applied, may cause discomfort to the wearer and/or produce an undesired localized pressure point on the skin of the wearer. Because high pressures are often required, such ridges could also eventually cause or exacerbate skin break down and result in ulcerations and other compromise of vascular flow and/or tissue integrity. When elastic bandages are used, the bandages overlap when applied, or may overlap more as they are worn, and create a localized pressure point that may cause skin irritation, breakdown, and ulceration.

Accordingly, there remains a need for compression stockings that are able to accurately achieve Class II, Class III, or greater compressive pressures at particular anatomical locations with proper pressure gradations and a smooth surface against the skin, while being easier to apply, than compression stockings and elastic compression bandages currently available. There is also a need for higher pressure compression stockings that are easier to correctly apply and that can be made efficiently and economically.

These needs, as well as other needs, are met by the present invention.

SUMMARY OF THE INVENTION

The present invention provides compression garments and bandages that overcome the disadvantages of currently available compression garments and elastic compression bandages and provide advantages to the wearer and caregiver.

One aspect of the present invention is a multilayer compression stocking system for use on a person's lower extremities. The compression stocking system comprises a plurality of layers including an underlayer and at least one overlayer. The underlayer may be worn next to the skin or over another stocking, bandage or garment and includes predetermined amounts of compressive pressure at discrete locations. The underlayer further includes alignment markings to assist a wearer in positioning the underlayer on their leg. The alignment markings may be located at the locations of compressive pressure or at different locations on the underlayer.

The overlayer or overlayers is/are applied over the underlayer. As discussed below with reference to other aspects and embodiments of the present invention, one or more of the overlayers may include alignment markings that may or may not correspond to the alignment markings on the underlayer. In an embodiment of the present invention, the overlayer is aligned simply by aligning the toe and heel portions of the underlayer and the overlayer. In alternative embodiments, as discussed below, alignment markings are utilized to align the overlayer and underlayer.

The overlayer may or may not include areas of compressive pressure depending on the application. The uppermost overlayer may be constructed and/or colored to have a pleasing cosmetic appearance.

Further details of possible embodiments of the underlayer and the overlayer are set forth below with reference to additional embodiments of the present invention.

Another aspect of the present invention is a multilayer compression stocking system comprising: a first layer, or underlayer, providing a predetermined amount of compressive pressure; at least one overlayer providing a predetermined amount of compressive pressure; and each layer including an alignment marking or markings so that the layers may be aligned, thereby aligning the areas of compressive pressure. Predetermined compressive pressures for each layer may be less than Class I pressure and may be Class I, Class II, and/or Class III pressures, or higher. More than one overlayer may be utilized to produce the compressive pressures desired. For example, an underlayer and additional overlayers may be layered to provide a total compressive pressure in a Class I range. As another example, an underlayer and two additional layers, each providing Class I compressive pressures, may be utilized to achieve Class III compressive pressures. The overlayer may be colored and/or constructed to provide an attractive appearance. For example, an overlayer may be provided in colors and/or patterns of conventional dress hosiery.

As will be recognized in the art, there is no standardized system for testing and measuring compressive pressures. The compressive pressure applied by stockings at a particular anatomical location may be determined and measured by various techniques. A commonly used system for measuring compressive pressures is a British system, which may be used with pressure testing equipment made by Instron and by Hatra. The British system divides compressive pressures into three levels, each level being referred to as a class. In the British system, Class I provides 14 to 19 mm Hg of compressive pressure, Class II provides 18 to 25 mm Hg of compressive pressure, and Class III provides 24 to 35 mm Hg of compressive pressure. Thus, at the point of greatest compressive pressure, a Class I stocking would provide 14 to 19 mm Hg of compressive pressure, a Class II stocking would provide 18 to 25 mm Hg of compressive pressure, and a Class III stocking would provide 24 to 35 mm Hg compressive pressure. Suggested preventative and therapeutic uses for each class of pressure are also defined by the British system. Another system for measuring compressive pressures is a German system, which may be used with testing equipment made by Holenstein. The German system categorizes compressive pressures between 20 and 30 mm Hg as Class I, between 30 and 40 mm Hg as Class II, and between 40 and 50 mm Hg as Class III.

A multilayer compression stocking system of the present invention may further comprise a final outer layer without medically therapeutic compressive pressures. The final outer layer may be colored and/or constructed to provide an attractive cosmetic appearance, for example, an appearance similar to non-compressive dress hosiery.

In use, an underlayer may be applied first to a wearer's leg and then an overlayer applied up and over the underlayer. Alignment markings on each layer may then be aligned to create the desired areas and amounts of compressive pressure and to ensure that the pressures are properly graduated, for example, in decreasing amounts up the leg. A final outer layer, if utilized, may then be applied up and over the compressive underlayer and overlayer.

A multilayer compression stocking of the present invention may be produced utilizing a circular knitting machine. Suitable yarns and knitting techniques include those set forth in the patents referred to above and incorporated herein by reference. It is generally preferable to construct the stocking without seams. Seamless construction provides the advantage of avoiding ridges or wrinkles, which may lead to deterioration of the skin. The multilayer compression stocking may be produced in different sizes, both in length and circumference, for use by a wide variety of people. Pressures graduations along the length of each layer would preferably be constructed the same so that the pressures are matched at the same location on each layer, ensuring the proper cumulative pressure effect and the proper pressure gradation when applied to a leg. The multilayer compression stocking may be any size, style, or length. For example, the multilayer compression stocking may be of knee length, or may extend above the knee in mid-thigh length, full-thigh length, or may be pantyhose. The underlayer could also be of a different length than the outer layer or layers. For example, the underlayer could be of knee length with the outer layer or layers thigh length.

A further aspect of the present invention is a multilayer compression bandage system. The bandage system comprises a plurality of layers including an underlayer and at least one overlayer. The underlayer may be worn next to the skin or over another bandage or garment and includes predetermined amounts of compressive pressure at discrete locations. The underlayer further includes alignment markings to assist a wearer in positioning the underlayer on their body. The alignment markings may be located at the locations of compressive pressure or at different locations on the underlayer.

The overlayer or overlayers is/are applied over the underlayer. As discussed below with reference to other aspects and embodiments of the present invention, one or more of the overlayers may include alignment markings that may or may not correspond to the alignment markings on the underlayer. In an embodiment of the present invention, the overlayer is aligned simply by aligning the top and bottom portions of the underlayer and the overlayer. In alternative embodiments, as discussed below, alignment markings are utilized to align the overlayer and underlayer.

The overlayer may or may not include areas of compressive pressure depending on the application. The uppermost overlayer may be constructed and/or colored to have a pleasing cosmetic appearance.

Further details of possible embodiments of the underlayer and the overlayer are set forth below with reference to additional embodiments of the present invention.

A further aspect of the present invention is a multilayer compressive bandage system comprising: a first layer, or underlayer, providing a predetermined amount of compressive pressure; at least one overlayer providing a predetermined amount of compressive pressure; and each layer including an alignment marking or markings so that the layers may be aligned, thereby aligning the areas of compressive pressure. Predetermined compressive pressures for each layer may be less than Class I pressure and may be Class I, Class II, and/or Class III pressures, or higher. More than one overlayer may be utilized to produce the compressive pressures desired. For example, an underlayer and two additional layers, each providing Class I compressive pressures, may be utilized to achieve Class III compressive pressures. The overlayer may be colored and/or constructed to provide an attractive appearance. For example, an overlayer may be provided in colors and/or patterns of conventional dress hosiery.

A multilayer compressive bandage system of the present invention may further comprise a final outer layer without medically therapeutic compressive pressures. The final outer layer may be colored and/or constructed to provide an attractive cosmetic appearance.

As will be understood by those of ordinary skill in the art, a multilayer compression system and method of the present invention may be utilized in multiple areas on a patient, including, but not limited to the leg; including upper and lower legs; foot; arm, including upper and lower arms; hand; torso; head and other locations where compression is desired. The amount of compressive force exerted by the multilayer compression bandage may be varied as described herein so as to provide the degree of compressive force desired at a particular location.

An advantage of the present invention is that a layering system allows a person to receive more compressive pressure than otherwise possible.

Another advantage of the present invention is that alignment markings or areas allow different layers to be correctly aligned to provide the desired compressive pressures at particular anatomical locations and proper pressure gradations along the length of the leg.

Another advantage of the present invention is that easier placement of compression stockings with higher total compressive pressures is allowed by the use of layers. As a result of such easier placement, compliance with use of higher pressure compression stockings as part of a medical regimen by elderly persons and those with compromised strength or mobility is enhanced.

Another advantage of the present invention is higher pressure compression stockings that are easier to correctly apply can be made efficiently and economically. An underlayer stocking is preferably constructed from nylon-covered spandex yarns alternating with relatively fine count nylon yarns to enhance ease of application by reducing friction and to reduce wrinkling upon application of the overlayer or overlayers.

An underlayer stocking is preferably constructed with mild or little compressive pressure in the toe area. Toe construction is preferably of a durable nylon yarn in the size range of fine to medium denier, or is reinforced through knitting techniques, to reduce the chance of cutting by toe nails. Construction with mild or little compressive pressure will generally decrease the risk of undesired pressure and reduce the chance of skin breakdown on the ends of the toes. The toe area is preferably constructed of high stretch modulus yarns so that the area will conform to the shape of the toes.

The instep of the underlayer stocking will generally be constructed to provide more compressive pressure than the toe area. Preferably the underlayer is constructed so that there is a smooth transition in material between the toe area and the instep area, without ridges, to minimize the chance, of producing an undesired localized pressure point on a wearer's skin. A smooth transition in construction may be accomplished, for example, by programming a knitting machine to enable a gradual change from one compression level to another, thereby eliminating a sharply defined line of pressure differential in the stocking.

To further reduce the chance of skin breakdown and to reinforce the stocking fabric, yarns with high strength and low coefficient of friction properties, such as Teflon, can also be incorporated into the fabric. Areas of the stocking including the toe, the top of the instep, and the heel may be reinforced in such a manner.

The heel area and ankle area of the underlayer stocking are preferably visually marked. Suitable marking techniques include using a knitted-in colored yarn, of a different color than the base yarn; a knit change; or marking by printing or applying a color to the heel area. Marking of the heel and ankle areas will assist in the alignment of the underlayer by allowing the marked heel area of the underlayer to be properly positioned on a wearer's foot.

Knitting between the toe area and the heel area of the underlayer will preferably reflect the anatomical shape of the foot in that area. Knitting between the ankle and calf will reflect the anatomical shape of the leg; for example, a typical hourglass shape may be utilized.

An underlayer stocking is preferably constructed so that it has compressive pressures in desired locations, including, the instep, heel, ankle, calf, knee, and/or thigh. Compressive pressures will generally gradually reduce from the distal portion of the stocking towards the proximal, or upper, portion of the stocking.

In order to facilitate correct placement of the underlayer stocking on the leg of a wearer, the stocking would be preferably knitted with yarns, and in a manner, so as to provide stretch in both the horizontal and vertical directions (i.e., at least two-way stretch). This feature will permit the stocking fabric to adjust for minor variations in anatomy in the ankle and/or knee areas.

As described above, according to the present invention, a multilayer compression stocking includes alignment markings to permit each stocking layer to be correctly placed on the wearer, and with respect to other stocking layers, so as to achieve the desired compressive pressure in the desired areas of the stocking and thus at desired locations on the leg of the wearer. The alignment markings may comprise a different color yarn, a knit change, printing, and/or other markings to differentiate discrete locations on a stocking. For example, during construction of a compressive pressure of the stocking, the knitting machine could be programmed to insert a yarn or provide a knit change at a desired location to produce an alignment marking. Preferably, the alignment marking will not introduce a rib or other wrinkle in the stocking layer that could cause a localized pressure point on a wearer's skin.

In general, it may be preferable for at least one set of alignment markings to correspond, or be located near, areas of greatest compressive pressure in a stocking. Thus, for example, alignment markings may be located near the heel and/or ankle region of each stocking layer. To facilitate and increase alignment, additional sets of alignment markings could be located in other areas, for example, the calf, instep, or other portions of the stocking. As an example, if pressure graduations are the same in each layer as preferred, alignment of the tops of the stocking layers, such as the tops of knee-length stocking layers, could also provide proper placement of stockings.

Additional stocking layers may be similar to the underlayer, with appropriate alignment markings and pressure characteristics and produced in similar manners. A final outer stocking layer may be colored and/or knitted in a fashion to provide an attractive cosmetic appearance. For example, a final outer stocking layer may be provided in colors and/or patterns of conventional dress hosiery.

An overlayer stocking is preferably constructed so that areas of compressive pressure have pressure characteristics and gradation that match the pressure characteristics and gradation of an underlayer. As an example, when compressive pressure is greatest at the ankle area for the underlayer, the greatest compressive pressure for the overlayer is preferably also at the ankle area, and both underlayer and overlayer are preferably aligned with each other and at the same place on the wearer's ankle. As discussed above, should the pressures along the length of the leg be misaligned, accurate placement of specifically desired higher pressures may not be achieved, resulting in a less effective stocking system, and a tourniquet effect could occur.

As will be realized from the foregoing discussion, the stocking layers in the system of the present invention may comprise separate articles. Alternatively, each of the stocking layers may be joined to create a multilayer compression stocking comprising a single article. For example, the multiple layers may be joined in the toe region.

A multilayer compression stocking of the present invention may be applied by first positioning the underlayer on the leg of a wearer. Each overlayer is then positioned over the underlayer, or the layer immediately underneath, by matching the toes, heels, alignment markings, and tops of the layers. Such successive placement of stocking layers by aligning like areas and alignment markings ensures proper positioning of compressive pressures in desired locations.

In the present invention, an underlayer may comprise a stocking with visually distinctive alignment markings in the toe, heel, and top areas. A distinctive visual appearance may be obtained, for example, through coloring, use of colored yarn, and/or a knitting change. An underlayer may additionally comprise an alignment marking, for example, at the most narrow point of the ankle. Use of the ankle alignment marking, and visually distinctive heel, toe, and top areas allow the underlayer to be properly positioned on a person's lower extremity.

An overlayer stocking may include visually apparent markings similar to those of an underlayer. Alternatively, an overlayer may include a visually distinctive heel region only. Alignment of the heel region and top of an overlayer with the heel region and top of an underlayer may provide sufficient alignment of the layers for a variety of applications.

Similar techniques may be utilized in the production and use of a multilayer compression bandage of the present invention. In certain embodiments, a non-circular knitting machine may be employed to produce multilayer compression bandages suitable for wrapping.

Those of ordinary skill in the art will appreciate the advantages and features of the present invention as described above and as is apparent from the detailed description below. As will be realized by those of skill in the art, many different embodiments of a multilayer compression stocking system according to the present invention are possible. Preferred embodiments of a multilayer compression stocking system will include one or more of the following features.

DETAILED DESCRIPTION

Systems and methods of a multilayer compression stocking and/or bandage according to the present invention provide a layering system that allows a person to receive higher compressive pressures, that can be correctly aligned to provide the desired compressive pressures at particular anatomical locations and proper pressure gradations along the length of the leg, and that can be applied with greater ease.

An example of an embodiment of the present invention is a multilayer compression stocking system comprising an underlayer and at least one overlayer, each of the layers having predetermined amounts of compressive pressure as discrete locations on the respective layer. Such an embodiment also includes at least one alignment marking on each layer. If multiple alignment markings are used, each marking may be positioned at a different location on a layer. Alignment markings on different layers correspond with similarly positioned alignment markings on each other layer, and, as such, can be aligned with corresponding markings on each other layer.

Figure 1:
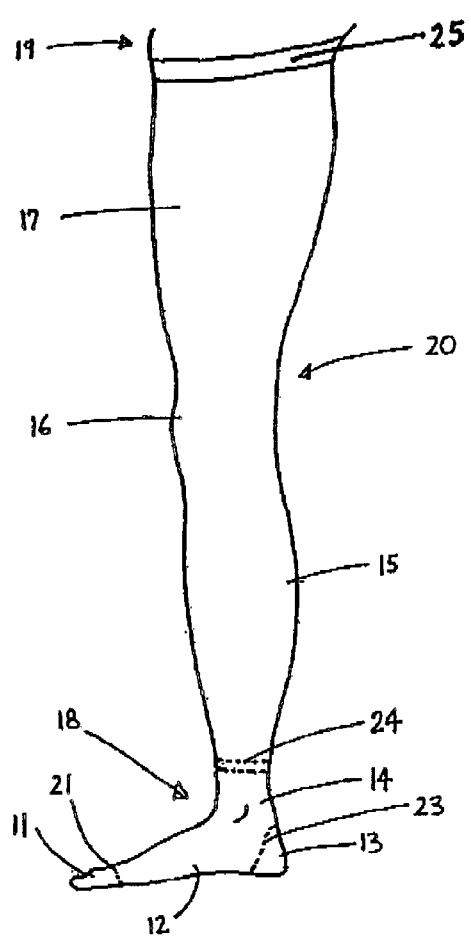
FIG. 1 is a perspective view of an embodiment of a compression stocking underlayer of the present invention.
Figure 2:
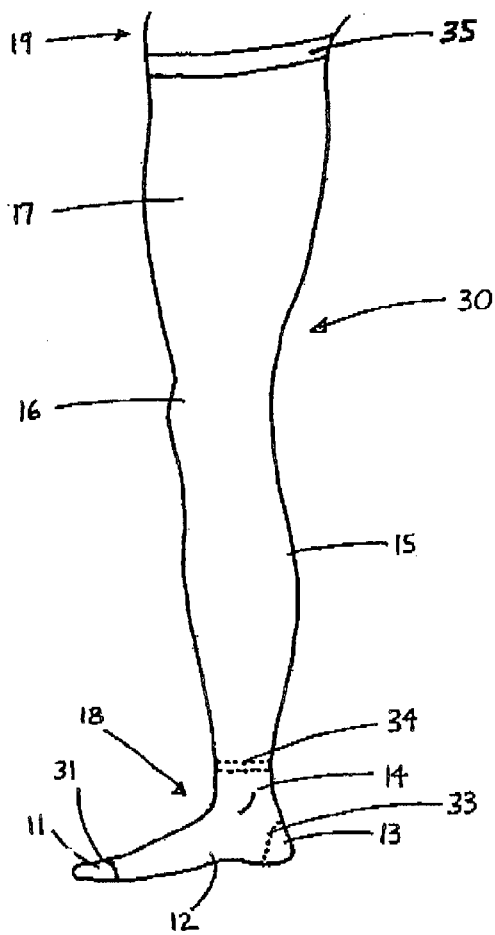
FIG. 2 is a perspective view of an embodiment of a compression stocking overlayer of the present invention.

FIGS. 1 and 2 illustrate an embodiment of a multilayer compression stocking system according to the present invention, including underlayer 20 (FIG. 1) and overlayer(s) 30 (FIG. 2). As shown in FIG. 1, underlayer 20 may comprise a stocking with visually distinctive alignment markings in the toe 11, heel 13, ankle 14, and proximal 19 areas. A distinctive visual appearance of alignment markings may be obtained, for example, through use of different colored yarns, a knitting change, printing, and/or colored markings. An underlayer may additionally comprise an alignment marking (24), for example, at the most narrow point of the ankle (14). Use of visually distinctive alignment markings of the toe 21, heel 23, ankle 24, and top 25 allow the underlayer to be properly positioned at the proper anatomical locations on a person's lower extremity.

Toe alignment markings 21 and 31 are positioned at the same location in toe area 11 on each of the underlayer 20 and overlayer(s) 30, respectively. In similar fashion, heel alignment markings 23 and 33 are positioned at the same location in heel area 13 on each of the underlayer 20 and overlayer(s) 30, respectively. Likewise, ankle alignment markings 24 and 34 are positioned at the same location in ankle area 14 on each of the underlayer 20 and overlayer(s) 30, respectively.

In such an embodiment, as illustrated in FIGS. 1 and 2 together, for example, alignment of alignment markings 31, 33, and 34 on overlayer(s) 30 with corresponding markings 21, 23, and 24 on underlayer 20 allows accurate alignment of discrete locations of compressive pressure on each layer. As a result, specific higher cumulative pressures can be accurately applied to particular anatomical locations on a leg.

In an alternative embodiment, an overlayer may include a visually distinctive heel region 13 only. In such an embodiment, alignment of the heel region 13 and top 35 of overlayer 30 with the heel region 13 and top 25 of an underlayer 20 may provide sufficient alignment of the layers for a variety of applications.

Systems and methods of an embodiment of the present invention may also comprise pressure graduations along the length of each of underlayer 20 and overlayer(s) 30. Pressure graduations are preferably the same along the length of each layer such that compressive pressures can be matched at each anatomical location, for example, at instep 12, heel 13, ankle 14, calf 15, knee 16, and thigh 17. Aligning the same pressure graduations along the length of each layer can also ensure the proper cumulative pressure graduation along the length of a layered stocking system when the layers are applied to a leg.

An embodiment of the present invention may also include the greatest amount of compressive pressure at a predetermined distal portion of each of the underlayer and overlayer(s). In addition, one of the alignment markings of each of the underlayer and overlayer(s) may be located at a predetermined area of greatest compressive pressure. Referring to FIGS. 1 and 2, underlayer 20 and overlayer(s) 30 may be constructed so as to provide the greatest amount of compressive pressure at distal portion 18. Ankle alignment markings 24 and 34 would thus be located at the predetermined area of greatest compressive pressure on each of the underlayer 20 and overlayer(s) 30. By aligning alignment markings 24 and 34, the greatest amount of compressive pressure at predetermined distal portion 18 of each of the underlayer and overlayer(s) would be aligned, further ensuring that the amounts of compressive pressure decrease from predetermined distal portion 18 to proximal portion 19 along the length of a wearer's leg.

In an embodiment of a multilayer compression stocking system of the present invention, predetermined amounts of compressive pressure of each of the underlayer 20 and overlayer(s) 30 may comprise less than Class I pressure, Class I, Class II, and/or Class III pressures, or higher compressive pressures, as described above. Layering of compressive pressure stockings in a multilayer compression stocking system will produce a cumulative pressure effect and allow higher compressive pressures when applied to a wearer's leg than otherwise attainable.

With higher compressive pressures attainable in a multilayer compression stocking system, construction of the layers may include features to reduce the risk of localized pressure points on a wearer's skin. For example, each of the underlayer 20 and overlayer(s) 30 may comprise a toe portion 11 constructed with mild or little compressive pressure and having a high stretch modulus so that toe area 11 will conform to the shape of the wearer's toes. Each of the layers may also comprise construction having at least a two-way stretch. For example, providing for stretch in both the horizontal and vertical directions will allow the stocking fabric to adjust for minor variations in anatomy in ankle area 14 and knee area 16. Each of the layers may also comprise construction having the shape of the anatomy of the lower extremities, including toe 11, instep 12, heel 13, ankle 14, calf 15, knee 16, and thigh 17, to provide for a smoother, more conforming fit of each stocking layer.

Each of the underlayer 20 and overlayer(s) 30 preferably have seamless construction. In particular, construction in and between toe area 11 and instep area 12 of each layer should be smooth so as to decrease any risk of localized pressure points which may lead to skin breakdown.

While underlayer 20 and overlayer 30 are depicted as full-thigh length layers, stockings of knee-length, mid-thigh length, and pantyhose length may also be utilized in accordance with the present invention.

In an alternative embodiment, each of the underlayer 20 and overlayer(s) 30 may be constructed so as to be joined in the toe portion 11. Such an arrangement would facilitate keeping the multiple layers together so that matching layers would be used in conjunction with each other each time they are applied.

In an embodiment of a multilayer compression stocking system of the present invention, one of the overlayer(s) 30 may be an outermost overlayer. Such an outermost layer may be colored and/or constructed to provide an attractive cosmetic appearance. In an alternative embodiment, a non-compressive final outer layer may be placed over the outermost overlayer. Such a non-compressive final outer layer may be colored and/or constructed to provide an attractive cosmetic appearance.

Figure 3:
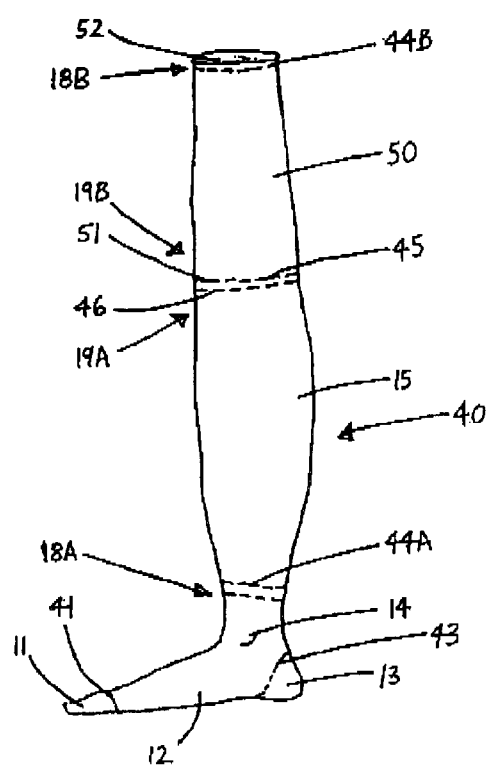
FIG. 3 is a perspective view of an embodiment of a compression stocking underlayer and overlayer of the present invention, illustrating an overlayer bottom foldably attached to an underlayer top.
Figure 4:
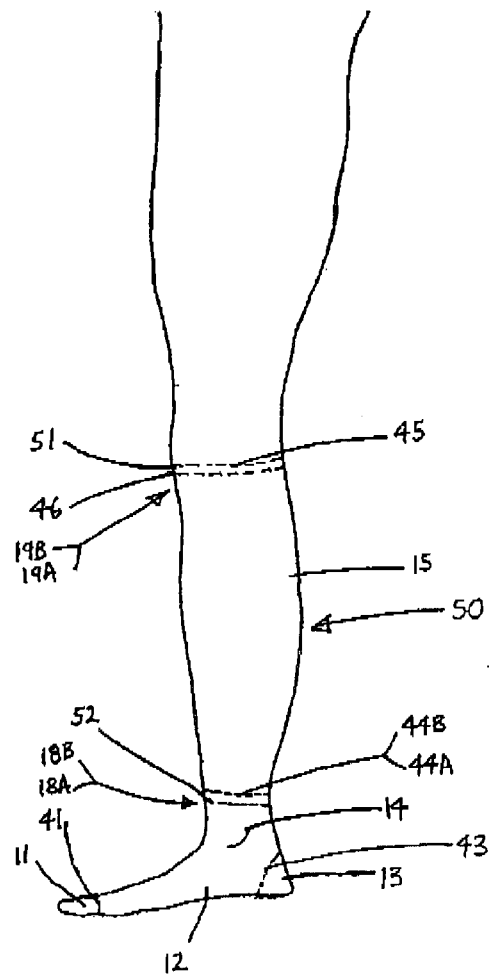
FIG. 4 is a perspective view of the embodiment of the multilayer compression stocking of FIG. 3 with the overlayer folded over the underlayer.

FIGS. 3 and 4 illustrate an embodiment of a multilayer compression stocking system according to the present invention, including an overlayer 50 foldably attached to an underlayer 40. As shown in FIG. 3, underlayer 40 may comprise a knee-length stocking with visually distinctive alignment markings in the toe 11, heel 13, ankle 14, and calf 15 areas. A distinctive visual appearance of alignment markings may be obtained, as described above, through use of different colored yarns, a knitting change, printing, and/or colored markings, for example. An underlayer may additionally comprise an alignment marking (44A), for example, at the most narrow point of ankle 14. Use of visually distinctive toe 41, heel 43, ankle 44A, and knee 45 alignment markings allow the underlayer to be properly positioned at the corresponding anatomical locations on a person's lower extremity.

In FIG. 3, underlayer 40 is shown as having a top 46 in proximal area 19A. Overlayer 50 is shown as having a bottom 51 in proximal area 19B, and a top 52 at distal portion 18B. Bottom 51 of overlayer 50 is attached to top 46 of underlayer 40 at knee alignment marking 45.

FIG. 4 depicts overlayer 50 folded down and in position over underlayer 40. To achieve proper therapeutic positioning, top 52 of overlayer 50 is folded downwardly so that ankle alignment marking 44B of overlayer 50 aligns with ankle alignment marking 44A of underlayer 40. As such, ankle alignment markings 44A and 44B are aligned at the same location in ankle area 14.

In such an embodiment, as illustrated in FIGS. 3 and 4, for example, positioning knee alignment marking 45 above calf 15 and aligning ankle alignment markings 44A and 44B in ankle area 14 allows accurate alignment of discrete locations of compressive pressure on each layer. As a result, specific higher cumulative pressures can be accurately applied to particular anatomical locations on a leg.

Systems and methods of an embodiment of the present invention, as illustrated in FIGS. 3 and 4, may also comprise pressure graduations along the length of each of underlayer 40 and overlayer 50. Pressure graduations are preferably the same along the length of each layer such that compressive pressures can be matched at specific anatomical locations, for example, at ankle 14 and calf 15. Aligning the same pressure graduations along the length of each layer can also ensure the proper cumulative pressure graduation along the length of a layered stocking system when the layers are applied to a leg.

An embodiment of the present invention may also include the greatest amount of compressive pressure at a predetermined distal portion of each of the underlayer and overlayer. In addition, one of the alignment markings of each of the underlayer and overlayer may be located at a predetermined area of greatest compressive pressure. Referring to FIGS. 3 and 4, underlayer 40 and overlayer 50 may be constructed so as to provide the greatest amount of compressive pressure at distal portions 18A and 18B, respectively. Ankle alignment markings 44A and 44B would thus be located at a predetermined area of greatest compressive pressure on each of the underlayer 40 and overlayer 50. By aligning alignment markings 44A and 44B, the greatest amount of compressive pressure at predetermined distal portions 18A and 18B of the underlayer 40 and overlayer 50, respectively, would be aligned, further ensuring that the amounts of compressive pressure decrease from predetermined distal portions 18A and 18B to proximal portions 19A and 19B along the length of a wearer's leg.

In an embodiment of a multilayer compression stocking system of the present invention, predetermined amounts of compressive pressure of each of the underlayer 40 and overlayer 50 may comprise less than Class I pressure, Class I, Class II, and/or Class III pressures, or higher compressive pressures, as described above. Layering of compressive pressure stockings in a multilayer compression stocking system will produce a cumulative pressure effect and allow higher compressive pressures when applied to a wearer's leg than otherwise attainable.

With higher compressive pressures attainable in a multilayer compression stocking system, construction of the layers may include features to reduce the risk of localized pressure points on a wearer's skin. For example, each of the layers may also comprise construction having at least a two-way stretch to allow for minor variations in anatomy, as in ankle area 14, as well as to facilitate downward folding of overlayer 50 over underlayer 40. The underlayer may also comprise construction having the shape of the anatomy of the lower extremities, including toe 11, instep 12, heel 13, ankle 14, and calf 15, to provide for a smoother, more conforming fit.

As discussed above, underlayer 40 and overlayer 50 would preferably have seamless construction. In particular, construction in and between toe area 11 and instep area 12 of underlayer 40 should be smooth so as to decrease any risk of localized pressure points which may lead to skin breakdown.

While underlayer 40 and overlayer 50 are depicted as knee length layers, stockings of other lengths may also be utilized in accordance with the present invention as embodied in FIGS. 3 and 4. As described above, an overlayer may be colored and/or constructed to provide an attractive cosmetic appearance.

An embodiment of a method of applying a multilayer compression stocking system of the present invention on a person's lower extremity may comprise: positioning on the lower extremity a compressive pressure underlayer 20 having at least one alignment marking, each underlayer alignment marking positioned at a different location on the underlayer 20 and corresponding to an anatomical location on the lower extremity; aligning each underlayer alignment marking with the corresponding anatomical location on the lower extremity; positioning over the underlayer 20 at least one compressive pressure overlayer 30 having at least one alignment marking, each overlayer alignment marking corresponding to a different one of the underlayer alignment markings; and aligning each overlayer alignment marking with each corresponding underlayer alignment marking. Therein, each of the underlayer 20 and overlayer(s) 30 may have predetermined amounts of compressive pressure at discrete locations, as described above. In such an embodiment, where one of the overlayer(s) 30 is an outermost overlayer, the present invention may further comprise positioning a non-compressive final outer layer over the outermost overlayer.

Another embodiment of a method of applying a multilayer compression stocking system of the present invention on a person's lower extremity may comprise: providing a compressive pressure underlayer 40 having a top 46 and at least one alignment marking, each underlayer alignment marking positioned at a different location on the underlayer and corresponding to a different anatomical location on the lower extremity; positioning the compressive pressure underlayer 40 on the lower extremity; aligning each underlayer alignment marking, for example ankle alignment marking 44A, with the corresponding anatomical location, for example ankle 14, on the lower extremity; providing a compressive pressure overlayer 50 having a top 52, a bottom 51, the overlayer bottom 51 foldably attached to the underlayer top 46, and at least one alignment marking, for example ankle alignment marking 44B, each overlayer alignment marking corresponding to a different one of the underlayer alignment markings; downwardly folding overlayer 50 over the underlayer 40; and aligning each overlayer alignment marking with each corresponding underlayer alignment marking.

In such embodiments of methods of applying a multilayer compression stocking system according to the present invention, each of the underlayer 40 and overlayer 50, for example, may have predetermined amounts of compressive pressure at discrete locations. Each of the underlayer 40 and overlayer 50 may have the same pressure graduations along its respective length from distal portions 18A and 18B to proximal portions 19A and 19B, so that the amounts of compressive pressure decrease from a predetermined distal portion to the proximal portion along the length of each of the underlayer 40 and overlayer 50.

Although the present invention has been described with reference to particular embodiments, it should be recognized that these embodiments are merely illustrative of the principles of the present invention. Those of ordinary skill in the art will appreciate that the system of the present invention may be implemented in other ways and embodiments. Accordingly, the description herein should not be read as limiting the present invention, as other embodiments also fall within the scope of the present invention.

What is claimed is:

1. A multilayer compression stocking system for use on a person's lower extremities, comprising:

a plurality of layers including an underlayer and at least one overlayer;

the underlayer having predetermined amounts of compressive pressure at discrete locations on the underlayer and having at least one alignment marking, each underlayer alignment marking positioned at a different location on the underlayer corresponding to a different anatomical location on the lower extremities;

each of the underlayer and the at least one overlayer further comprising a length with pressure graduations along the length, the pressure graduations being the same along the length of each of the underlayer and the at least one overlayer; and each underlayer and overlayer further comprising a toe portion, wherein the toe portion of at least one of the underlayer and overlayers has a high stretch modulus, and wherein when the underlayer is applied to the lower extremities, each underlayer alignment marking is aligned with the corresponding anatomical location, and the at least one overlayer is applied over the underlayer, the discrete locations of compressive pressure on the underlayer are aligned with the same pressure on the at least one overlayer to provide an expected cumulative compressive pressure at each anatomical location on the person's lower extremities.

2. The multilayer compression stocking system of claim 1, each underlayer and overlayer having an instep portion, wherein at least one of the underlayer and overlayers further comprises a smooth construction from the toe portion to the instep portion therein.

3. A multilayer compression stocking system for use on a person's lower extremities, comprising:

a plurality of layers including an underlayer and at least one overlayer;

the underlayer having predetermined amounts of compressive pressure at discrete locations on the underlayer;

at least one of the overlayers having predetermined amounts of compressive pressure at discrete locations thereon;

the underlayer having at least one alignment marking, each underlayer alignment marking positioned at a different location on the underlayer;

each overlayer having at least one alignment marking, each overlayer alignment marking corresponding to a different one of the underlayer alignment markings;

each of the underlayer and the at least one overlayer further comprising a length with proximal and distal portions and with pressure graduations along the length, the pressure graduations being the same along the length of each of the underlayer and the at least one overlayer; and each underlayer and overlayer further comprising a toe portion, wherein the toe portion of at least one of the underlayer and overlayers has a high stretch modulus, and wherein when the at least one overlayer is applied over the underlayer and the overlayer alignment markings are aligned with corresponding underlayer alignment markings, the discrete locations of the same compressive pressure on the underlayer and each overlayer are aligned to provide an expected cumulative compressive pressure at each discrete location.

4. The multilayer compression stocking system of claim 3, each underlayer and overlayer having an instep portion, wherein at least one of the underlayer and overlayers further comprises a smooth construction from the toe portion to the instep portion therein.

5. The multilayer compression stocking system of claim 3, wherein the underlayer and each overlayer are joined in the toe portion.

6. A method of applying a multilayer compression stocking system on a person's lower extremity, comprising:

providing an underlayer having predetermined amounts of compressive pressure at discrete locations and at least one alignment marking, each underlayer alignment marking positioned at a different location on the underlayer and corresponding to a different anatomical location on the lower extremity;

positioning the underlayer on the lower extremity;

aligning each underlayer alignment marking with the corresponding anatomical location on the lower extremity;

providing at least one overlayer having predetermined amounts of compressive pressure at discrete locations and having at least one alignment marking, each overlayer alignment marking corresponding to a different one of the underlayer alignment markings, each underlayer and overlayer having a length with proximal and distal portions, the underlayer having pressure graduations along its length, each overlayer having pressure graduations along its length, the pressure graduations along the length of each overlayer being the same as the pressure graduations along the length of the underlayer, the amount of compressive pressure being greatest at the distal portion of the underlayer and each overlayer so that the amount of compressive pressure decreases from the distal portion to the proximal portion along the length of the underlayer and each overlayer;

positioning one of the at least one overlayer over the underlayer; and aligning each overlayer alignment marking with each corresponding underlayer alignment, wherein the pressure graduations on the underlayer and the same pressure graduations on the at least one overlayer are aligned to provide an expected cumulative compressive pressure at each anatomical location on the person's lower extremity.

7. A multilayer compression stocking system for use on a person's lower extremities, comprising:

a plurality of layers including an underlayer and an overlayer;

the underlayer and the overlayer each having predetermined amounts of compressive pressure at discrete locations thereon;

each underlayer and overlayer having a length with proximal and distal portions, the underlayer having pressure graduations along its length and the overlayer having the same pressure graduations along its length as the underlayer;

the underlayer having at least one alignment marking, each underlayer alignment marking positioned at a different location on the underlayer;

the overlayer having at least one alignment marking, each overlayer alignment marking corresponding to a different one of the underlayer alignment markings; and the underlayer having a top, the overlayer having a top and a bottom, and the overlayer bottom foldably attached to the underlayer top, wherein the overlayer is downwardly folded over the underlayer to align the overlayer alignment markings with the corresponding underlayer alignment markings to align the discrete locations of compressive pressure on the underlayer and the discrete locations of the same compressive pressure on the overlayer to provide an expected cumulative compressive pressure at each discrete location.

8. The multilayer compression stocking system of claim 7, wherein the amount of compressive pressure is greatest at the distal portion of each underlayer and overlayer so that the amount of compressive pressure decreases from the distal portion to the proximal portion along the length of each underlayer and overlayer.

9. The multilayer compression stocking system of claim 8, wherein one of the underlayer alignment markings and the corresponding overlayer alignment marking are located at the distal portion of the underlayer and each overlayer where the amount of compressive pressure is greatest.

10. The multilayer compression stocking system of claim 7, wherein the predetermined amounts of compressive pressure of each underlayer and overlayer range from 14 mm Hg to about 50 mm Hg.

11. The multilayer compression stocking system of claim 7, wherein each underlayer and overlayer further comprises a toe portion, at least one toe portion having a high stretch modulus.

12. The multilayer compression stocking system of claim 11, the underlayer having an instep portion, wherein the underlayer further comprises a smooth construction from the toe portion to the instep portion.

13. The multilayer compression stocking system of claim 7, wherein the underlayer further comprises a heel portion and one of the at least one alignment marking of the underlayer is located on the heel portion.

14. The multilayer compression stocking system of claim 7, each of the underlayer and overlayer having a shape, wherein the underlayer further comprises knit construction having the shape of the anatomy of the lower extremities.

15. The multilayer compression stocking system of claim 7, wherein at least one of the underlayer and overlayer further comprises construction having at least two-way stretch.

16. The multilayer compression stocking system of claim 7, wherein at least one of the underlayer and overlayer further comprises seamless construction.

17. The multilayer compression stocking system of claim 7, wherein the underlayer alignment markings and the overlayer alignment markings comprise different colored yarns, a knit change, printing, and/or colored markings.

18. The multilayer compression stocking system of claim 7, wherein the overlayer is colored to provide a cosmetic appearance.

19. The multilayer compression stocking system of claim 18, wherein the colored overlayer further comprises construction to provide a cosmetic appearance.

20. The multilayer compression stocking system of claim 7, wherein the overlayer is constructed to provide a cosmetic appearance.

21. The multilayer compression stocking system of claim 7, wherein the length of at least one of the underlayer and overlayer is knee-length.

22. A multilayer compression stocking system for use on a person's lower extremities, comprising:

an underlayer having predetermined amounts of compressive pressure at discrete locations on the underlayer;

an overlayer having predetermined amounts of compressive pressure at discrete locations on the overlayer;

each of the underlayer and overlayer having a length with proximal and distal portions, the underlayer having pressure graduations along its length, the overlayer having pressure graduations along its length;

the pressure graduations along the length of the overlayer are the same as the pressure graduations along the length of the underlayer;

the amount of compressive pressure is greatest at the distal portion of each of the underlayer and overlayer;

the amount of compressive pressure decreases from the distal portion to the proximal portion along the length of each of the underlayer and overlayer;

the underlayer having at least one alignment marking, each underlayer alignment marking positioned at a different location on the underlayer;

the overlayer having at least one alignment marking, each overlayer alignment marking corresponding to a different one of the underlayer alignment markings; and the underlayer having a top, the overlayer having a top and a bottom, and the overlayer bottom foldably attached to the underlayer top, folding the overlayer is downwardly folded over the underlayer to align the overlayer alignment markings with the corresponding underlayer alignment markings to align the discrete locations of compressive pressure on the underlayer and the discrete locations of the same compressive pressure on the overlayer so that the distal portion of each of the underlayer and the overlayer where the amount of compressive pressure is greatest are aligned and so that the same pressure graduations along the length of each of the underlayer and the overlayer are aligned to provide an expected cumulative compressive pressure at each discrete location.

23. A method of applying a multilayer compression stocking system on a person's lower extremity, comprising:

providing a compressive pressure underlayer having a length with proximal and distal portions with pressure graduations along the length, a top, and at least one alignment marking, each underlayer alignment marking positioned at a different location on the underlayer and corresponding to a different anatomical location on the lower extremity;

positioning the compressive pressure underlayer on the lower extremity;

aligning each underlayer alignment marking with the corresponding anatomical location on the lower extremity;

providing a compressive pressure overlayer having a length with proximal and distal portions with pressure graduations along the length, the pressure graduations being the same along the length of the underlayer and the overlayer, a top, a bottom, the overlayer bottom foldably attached to the underlayer top, and at least one alignment marking, each overlayer alignment marking corresponding to a different one of the underlayer alignment markings;

downwardly folding the overlayer over the underlayer; and aligning each overlayer alignment marking with each corresponding underlayer alignment marking, wherein the pressure graduations on the underlayer and the same pressure graduations on the overlayer are aligned to provide an expected cumulative compressive pressure at each anatomical location on the person's lower extremity.

24. The method of applying a multilayer compression stocking system of claim 23, wherein at least one of the underlayer and overlayer has predetermined amounts of compressive pressure at discrete locations.

25. The method of applying a multi layer compression stocking system of claim 24, wherein the predetermined amounts of compressive pressure range from 20–30 mm Hg, 30–40 mm Hg, or 40–50 mm Hg.

26. The method of applying a multilayer compression stocking system of claim 23, wherein the amount of compressive pressure is greatest at the distal portion of each of the underlayer and overlayer so that the amount of compressive pressure decreases from the distal portion to the proximal portion along the length of each of the underlayer and overlayer.

27. The method of applying a multilayer compression stocking system of claim 26, wherein one of the underlayer alignment markings and the corresponding overlayer alignment marking are located at the distal portion of the underlayer and each overlayer where the amount of compressive pressure is greatest.

28. A method of applying a multilayer compression stocking system on a person's lower extremity, comprising:

providing a compressive pressure underlayer having a top, predetermined amounts of compressive pressure at discrete locations, and at least one alignment marking, each underlayer alignment marking positioned at a different location on the underlayer and corresponding to a different anatomical location on the lower extremity;

positioning the underlayer on the lower extremity;

aligning each underlayer alignment marking with the corresponding anatomical location on the lower extremity;

providing a compressive pressure overlayer having a top, a bottom, the overlayer bottom foldably attached to the underlayer top, at least one alignment marking, each overlayer alignment marking corresponding to a different one of the underlayer alignment markings, and predetermined amounts of compressive pressure at discrete locations, each of the underlayer and the overlayer having a length with proximal and distal portions, the underlayer having pressure graduations along its length, the overlayer having pressure graduations along its length, the pressure graduations along the length of the overlayer are the same as the pressure graduations along the length of the underlayer, the amount of compressive pressure being greatest at the distal portion of each of the underlayer and overlayer so that the amount of compressive pressure decreases from the distal portion to the proximal portion along the length of each of the underlayer and overlayer;

downwardly folding the overlayer over the underlayer; and aligning each overlayer alignment marking with each corresponding underlayer alignment marking, wherein the discrete locations of compressive pressure on the underlayer and the discrete locations of the same compressive pressure on the overlayer are aligned so that the distal portion of each of the underlayer and the overlayer where the amount of compressive pressure is greatest are aligned and so that the same pressure graduations along the length of each of the underlayer and the overlayer are aligned to provide an expected cumulative compressive pressure at each discrete location on the underlayer and the overlayer and thereby at each anatomical location on the person's lower extremity.

29. A multilayer compression bandage system comprising:

an underlayer having predetermined amounts of compressive pressure at discrete locations on the underlayer;

at least one overlayer having predetermined amounts of compressive pressure at discrete locations thereon;

the underlayer having at least one alignment marking, each underlayer alignment marking positioned at a different location on the underlayer;

each overlayer having at least one alignment marking, each overlayer alignment marking corresponding to a different one of the underlayer alignment markings; and each of the underlayer and the at least one overlayer further comprising a length with proximal and distal portions and with pressure graduations along the length, the pressure graduations being the same along the length of each of the underlayer and the at least one overlayer, wherein when the at least one overlayer is applied over the underlayer and the overlayer alignment markings are aligned with corresponding underlayer alignment markings, the discrete locations of the same compressive pressure on the underlayer and each overlayer are aligned to provide an expected cumulative compressive pressure at each discrete location.

30. The multilayer compression bandage system of claim 29, wherein the amount of compressive pressure is greatest at the distal portion of each of the underlayer and overlayer so that the amount of compressive pressure decreases from the distal portion to the proximal portion along the length of each of the underlayer and overlayer.

31. The multilayer compression bandage system of claim 29, wherein the predetermined amounts of compressive pressure range from 20–30 mm Hg, 30–40 mm Hg, or 40–50 mm Hg.

32. A method for preventing and treating a medical condition using compressive pressure, comprising:

positioning on a person's body a compressive pressure underlayer having a length with predetermined amounts of compressive pressure graduated at discrete locations along the length and at least one alignment marking, each underlayer alignment marking positioned at a different location on the underlayer and corresponding to a different anatomical location on the body;

aligning each underlayer alignment marking with the corresponding anatomical location;

positioning over the underlayer at least one compressive pressure overlayer having a length with predetermined amounts of compressive pressure graduated at discrete locations along the length, the pressure graduations being the same along the length of the underlayer and the at least one overlayer and at least one alignment marking, each overlayer alignment marking corresponding to a different one of the underlayer alignment markings; and aligning each overlayer alignment marking with each corresponding underlayer alignment marking, wherein the pressure graduations on the underlayer and the same pressure graduations on the at least one overlayer are aligned to provide an expected cumulative compressive pressure at each anatomical location to facilitate healing.

33. The method of claim 32, wherein the medical condition comprises edema.

34. The method of claim 32, wherein the medical condition comprises emboli.

35. The method of claim 32, wherein the medical condition comprises thrombophlebitis.

36. The method of claim 32, wherein the medical condition comprises an ulcer.

37. The method of claim 32, further comprising:

applying a dressing to the anatomical location affected by the medical condition; and positioning the compressive pressure underlayer over the dressing, wherein the dressing is held in place.

38. The method of claim 37, wherein the dressing comprises therapeutic agents.

39. The method of claim 32, one of the at least one overlayer being an outermost overlayer, wherein the outermost overlayer is colored to provide a cosmetic appearance.

40. The method of claim 32, wherein the method is performed by the person on whose body the compressive pressure underlayer and the at least one compressive pressure overlayer are positioned.

* * * * *